(12) United States Patent
Sartor et al.

(10) Patent No.: US 9,913,653 B2
(45) Date of Patent: Mar. 13, 2018

(54) DEVICES, SYSTEMS, AND METHODS FOR TISSUE MORCELLATION

(71) Applicant: COVIDIEN LP, Mansfield, MA (US)

(72) Inventors: Joe D. Sartor, Longmont, CO (US); Arlen K. Ward, Thornton, CO (US)

(73) Assignee: Covidien LP, Mansfield, MA (US)

( * ) Notice: Subject to any disclaimer, the term of this patent is extended or adjusted under 35 U.S.C. 154(b) by 634 days.

(21) Appl. No.: 14/325,550

(22) Filed: Jul. 8, 2014

(65) Prior Publication Data

US 2015/0018815 A1    Jan. 15, 2015

Related U.S. Application Data

(60) Provisional application No. 61/845,188, filed on Jul. 11, 2013, provisional application No. 61/882,714, filed on Sep. 26, 2013.

(51) Int. Cl.
*A61B 17/32* (2006.01)
*A61B 18/12* (2006.01)
(Continued)

(52) U.S. Cl.
CPC .... *A61B 17/32002* (2013.01); *A61B 17/3205* (2013.01); *A61B 17/32053* (2013.01);
(Continued)

(58) Field of Classification Search
CPC ......... A61B 18/04; A61B 18/12; A61B 18/14; A61B 18/1402; A61B 18/1405; A61B 18/148; A61B 18/1482; A61B 18/1485; A61B 2018/00601; A61B 2018/1407; A61B 2018/144; A61B 2018/1497; A61B 17/32; A61B 17/320016; A61B 17/32002;
(Continued)

(56) References Cited

U.S. PATENT DOCUMENTS 5,403,276 A    4/1995  Schechter et al.
5,443,472 A    8/1995  Li
(Continued)

FOREIGN PATENT DOCUMENTS

EP        806183 A1    11/1997
GB       2327350 A     1/1999
(Continued)

OTHER PUBLICATIONS

U.S. Appl. No. 14/325,590, filed Jul. 8, 2014, inventor: Sartor.

*Primary Examiner* — Todd J Scherbel (57) ABSTRACT

A morcellator includes a housing, an elongated tube extending distally from the housing, and first and second electrodes. A distal end of the elongated tube is configured to cut tissue. The first electrode extends from the housing to the distal end of the elongated tube and is disposed around at least a portion of the distal end of the elongated tube. The second electrode extends distally beyond the first electrode. Another morcellator includes a housing, an elongated tube extending distally from the housing, and an oscillating mechanism. A distal end of the elongated tube includes opposing blade sections and at least one blunt section. The opposing blade sections are configured to cut tissue. The oscillating mechanism is configured to drive oscillation of the elongated tube to cut tissue with the blade sections.

10 Claims, 7 Drawing Sheets

(51) Int. Cl.
*A61B 18/14* (2006.01)
*A61B 17/3205* (2006.01)
*A61B 18/00* (2006.01)

(52) U.S. Cl.
CPC .. *A61B 18/1482* (2013.01); *A61B 17/320016* (2013.01); *A61B 18/1445* (2013.01); *A61B 2017/320024* (2013.01); *A61B 2018/00208* (2013.01); *A61B 2018/00601* (2013.01)

(58) Field of Classification Search
CPC .......... A61B 17/3205; A61B 17/32053; A61B 2017/320024
See application file for complete search history.

(56) References Cited

U.S. PATENT DOCUMENTS

| | | | |
|---|---|---|---|
| 5,520,634 A | 5/1996 | Fox et al. | |
| 5,569,284 A | 10/1996 | Young et al. | |
| 5,618,296 A | 4/1997 | Sorensen et al. | |
| 5,669,927 A | 9/1997 | Boebel et al. | |
| 5,746,760 A | 5/1998 | Humphrey, Jr. | |
| 5,916,198 A | 6/1999 | Dillow | |
| 6,039,748 A | 3/2000 | Savage et al. | |
| 6,045,566 A | 4/2000 | Pagedas | |
| 6,162,235 A | 12/2000 | Vaitekunas | |
| 6,468,228 B1 | 10/2002 | Topel et al. | |
| D535,748 S | 1/2007 | Wolf | |
| 7,156,839 B2 | 1/2007 | Bayer et al. | |
| 7,232,439 B2 | 6/2007 | Ciarrocca | |
| 7,850,684 B2 | 12/2010 | Marshall et al. | |
| 7,896,877 B2 | 3/2011 | Hall et al. | |
| 8,025,656 B2 | 9/2011 | Gruber et al. | |
| 8,100,928 B2 | 1/2012 | Nohilly et al. | |
| 8,152,820 B2 | 4/2012 | Mohamed et al. | |
| 8,308,746 B2 | 11/2012 | Pravong et al. | |
| 8,343,148 B2 | 1/2013 | Fleming et al. | |
| 8,608,764 B2 | 12/2013 | Ambardekar | |
| 8,652,156 B2 | 2/2014 | Holdgate et al. | |
| 8,900,230 B2 | 12/2014 | Jenkins et al. | |
| 9,066,724 B2 | 6/2015 | Jenkins | |
| 2005/0261676 A1 | 11/2005 | Hall et al. | |
| 2006/0089527 A1 | 4/2006 | Doll et al. | |
| 2008/0039880 A1 | 2/2008 | Nohilly et al. | |
| 2008/0039883 A1 | 2/2008 | Nohilly | |
| 2008/0058846 A1 | 3/2008 | Vosough | |
| 2008/0065129 A1 | 3/2008 | Batchelor et al. | |
| 2008/0103412 A1 | 5/2008 | Chin | |
| 2008/0135780 A1 | 6/2008 | Giering et al. | |
| 2008/0255597 A1 | 10/2008 | Pravong et al. | |
| 2009/0292281 A1 | 11/2009 | Fleming et al. | |
| 2010/0305566 A1 | 12/2010 | Rosenblatt et al. | |
| 2011/0184409 A1 | 7/2011 | Jenkins et al. | |
| 2011/0257651 A1* | 10/2011 | Jenkins | A61B 18/1485 606/48 |
| 2011/0264129 A1 | 10/2011 | Holdgate et al. | |
| 2012/0016399 A1 | 1/2012 | Poulsen | |
| 2012/0078038 A1 | 3/2012 | Sahney et al. | |
| 2013/0090642 A1 | 4/2013 | Shadduck et al. | |
| 2013/0123797 A1 | 5/2013 | Livneh | |
| 2013/0218186 A1 | 8/2013 | Dubois et al. | |

FOREIGN PATENT DOCUMENTS

| | | |
|---|---|---|
| GB | 2327351 A | 1/1999 |
| WO | 2009141579 A1 | 11/2009 |
| WO | 2014/123571 A1 | 8/2014 |

* cited by examiner

DEVICES, SYSTEMS, AND METHODS FOR TISSUE MORCELLATION

CROSS-REFERENCE TO RELATED APPLICATIONS

This application claims the benefit of, and priority to, U.S. Provisional patent application Ser. No. 61/845,188, which was filed on Jul. 11, 2013, and 61/882,714, which was filed on Sep. 26, 2013. This application is related to U.S. patent application Ser. No. 14/325,590, filed on Jul. 8, 2014. The entire contents of each of the above applications are hereby incorporated herein by reference.

BACKGROUND

1. Technical Field

The present disclosure relates to tissue morcellation and, more specifically, to minimally invasive tissue morcellators, morcellation systems, and tissue morcellation methods, which can be used for partial or total removal of body tissue or organs from the interior of the body.

2. Description of Related Art

In minimally invasive surgical procedures, operations are carried out within the body by using elongated instruments inserted through small entrance openings in the body. The initial opening in the body tissue to allow passage of instruments to the interior of the body may be a natural passageway of the body, or it can be created by a tissue-piercing instrument such as a trocar, or by a small incision into which a cannula is inserted.

Because the tubes, instrumentation, and any required punctures or incisions are relatively small, the surgery is less invasive as compared to conventional surgical procedures in which the surgeon is required to cut open large areas of body tissue. Therefore, minimally invasive surgery minimizes trauma to the patient and reduces patient recovery time and hospital costs.

Minimally invasive procedures may be used for partial or total removal of body tissue or organs from the interior of the body, e.g. myomectomy, nephrectomy, cholecystectomy, lobectomy, and other procedures including thoracic, abdominal, laparoscopic, and endoscopic procedures. During such procedures, it is common that a cyst, fibroid, myoma, tumor, or other affected tissue or organ needs to be removed via the access opening or through a cannula. Various types of entrapment devices have been disclosed to facilitate this procedure. In many procedures where cancerous tumors are removed, removal of the specimen in an enclosed environment is highly desirable to inhibit seeding of cancer cells (i.e., portions of cancer cells contacting healthy tissue).

Several minimally invasive surgical procedures require the bulk removal of body tissue or organs through a limited surgical opening. As such, the tissue needs to be morcellated within the body cavity into smaller pieces of tissue to facilitate removal with laparoscopic graspers or tenaculums through minimally invasive access ports or the morcellation tool itself. Examples of such tissue morcellation are found in myomectomies, laparoscopic nephrectomies, splenectomies, or laparoscopic supracervical hysterectomies.

In laparoscopic cases for bulk removal of tissue, it is advantageous to morcellate the tissue into large tissue segments, rather than small tissue breakups, which then can be removed in very few extraction steps. Apart from time savings, the removal of large tissue segments, rather than small tissue chips, also reduces the chance of cross-contamination with malignant or cancerous tissue. Specifically for the example of laparoscopic supra-cervical hysterectomies, it is advantageous to morcellate the severed uterus along the surface of the fundus (generating a continuous tissue peel), rather than to repetitively core into the bulk of the uterus (generating a multitude of tissue chips).

During morcellation, the opened jaws of the grasper or tenaculum may damage the edge of the cutting blade during manipulation, dramatically reducing its effectiveness and life.

SUMMARY

In aspects of the present disclosure, a morcellator is provided including a housing, an elongated tube, and first and second electrodes. The elongated tube extends distally from the housing and defines a longitudinal axis. The elongated tube defines a lumen therethrough. A distal end of the elongated tube is configured to cut through tissue. A portion of the first electrode extends from the housing to the distal end of the elongated tube. A portion of the first electrode is disposed around at least a portion of the circumference of the distal end of the elongated tube. Another portion of the first electrode returns from the distal end of the elongated tube to the housing. The first electrode is electrically coupled to an energy source. A first element of the second electrode extends distal to the first electrode. The second electrode is configured to couple to the energy source. An interior portion of the second electrode may be supported on a lip of the elongated tube.

In aspects of the present disclosure, a morcellator is provided including a housing, an elongated tube, and an oscillating mechanism. The elongated tube extends distally from the housing and defines a longitudinal axis. The elongated tube defines a lumen therethrough. A distal end of the elongated tube includes opposing blade sections and at least one blunt section. The opposing blade sections are configured to cut tissue. The oscillating mechanism is configured to drive oscillation of the elongated tube about the longitudinal axis.

In aspects of the present disclosure, the oscillating mechanism is configured to mechanically drive the elongated tube to oscillate. The oscillating mechanism can include a motor, a disc shaped cam, and a connecting member. The cam includes a distally extending cam pin affixed near the outer circumference of the cam. The connecting member includes a cam slot that is configured to receive the cam pin. The connecting member is fixed to the outer surface of the elongated tube and is configured to translate the rotation of the motor into oscillation of the elongated tube about the longitudinal axis.

In aspects of the present disclosure, the oscillating mechanism is configured to electromagnetically drive the elongated tube to oscillate. The oscillating mechanism can include one or more magnets affixed to the elongated tube and one or more corresponding solenoids. The solenoid(s) is configured to oscillate the elongated tube by generating magnetic fields that act upon the magnet(s).

In aspects of the present disclosure, a surgical kit includes a morcellator, a specimen retrieval bag, and a surgical instrument. The morcellator can be configured similar to any of the morcellators described herein. The specimen retrieval bag is configured to encapsulate tissue and/or organs to be removed from the body and to facilitate sealed removal of the morcellated tissue. The retrieval bag may be composed of a material to be resistant to puncture by the companion morcellator, e.g., any of the morcellators described herein.

The surgical instrument is configured to feed tissue to the distal end of the morcellator to facilitate tissue morcellation.

In aspects of the present disclosure a method of morcellating tissue includes inserting a surgical retrieval apparatus into a surgical site; encapsulating tissue to be morcellated within a specimen retrieval bag of the surgical retrieval apparatus, feeding tissue to be morcellated to the distal end of the morcellator with a surgical instrument, and activating the morcellator to morcellate tissue. Activating the morcellator can include energizing first and second electrodes of the morcellator to conduct energy between the electrodes and through tissue disposed therebetween to morcellate tissue. Activating the morcellator can include oscillating a distal cutting end of an elongated tube of the morcellator to morcellate tissue. Oscillating the distal cutting end can include mechanically driving the elongated tube to oscillate. Oscillating the distal cutting end can include electromagnetically driving the elongated tube to oscillate.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closest to the clinician and the term "distal" will refer to the portion of the device or component thereof that is furthest from the clinician.

Figures 1, 1A:
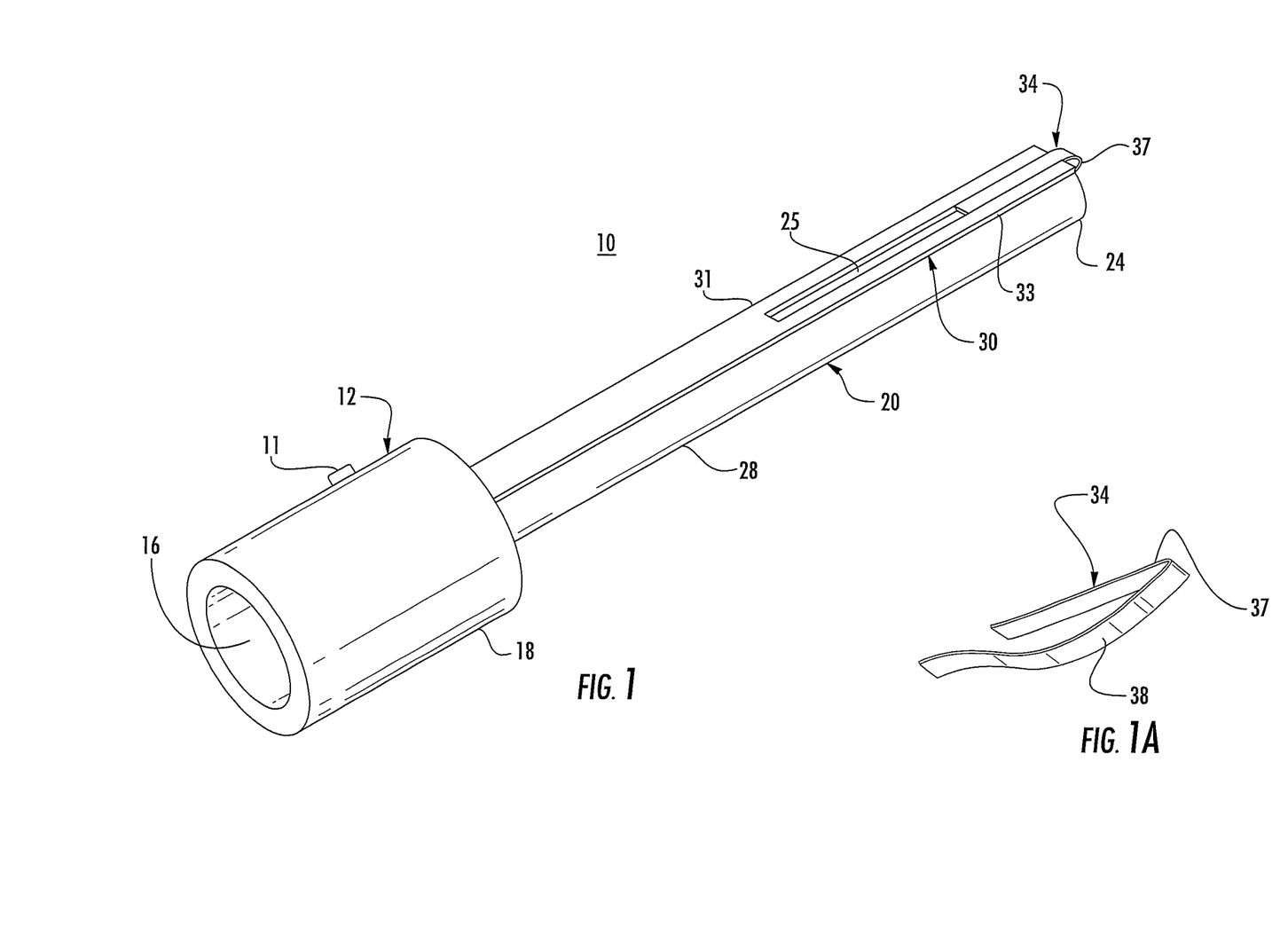
FIG. 1 is a rear perspective view of one illustrative embodiment of a morcellator in accordance with the present disclosure including an electrode.
FIG. 1A is a perspective view of an electrode of the morcellator shown in FIG. 1.
Figure 2:
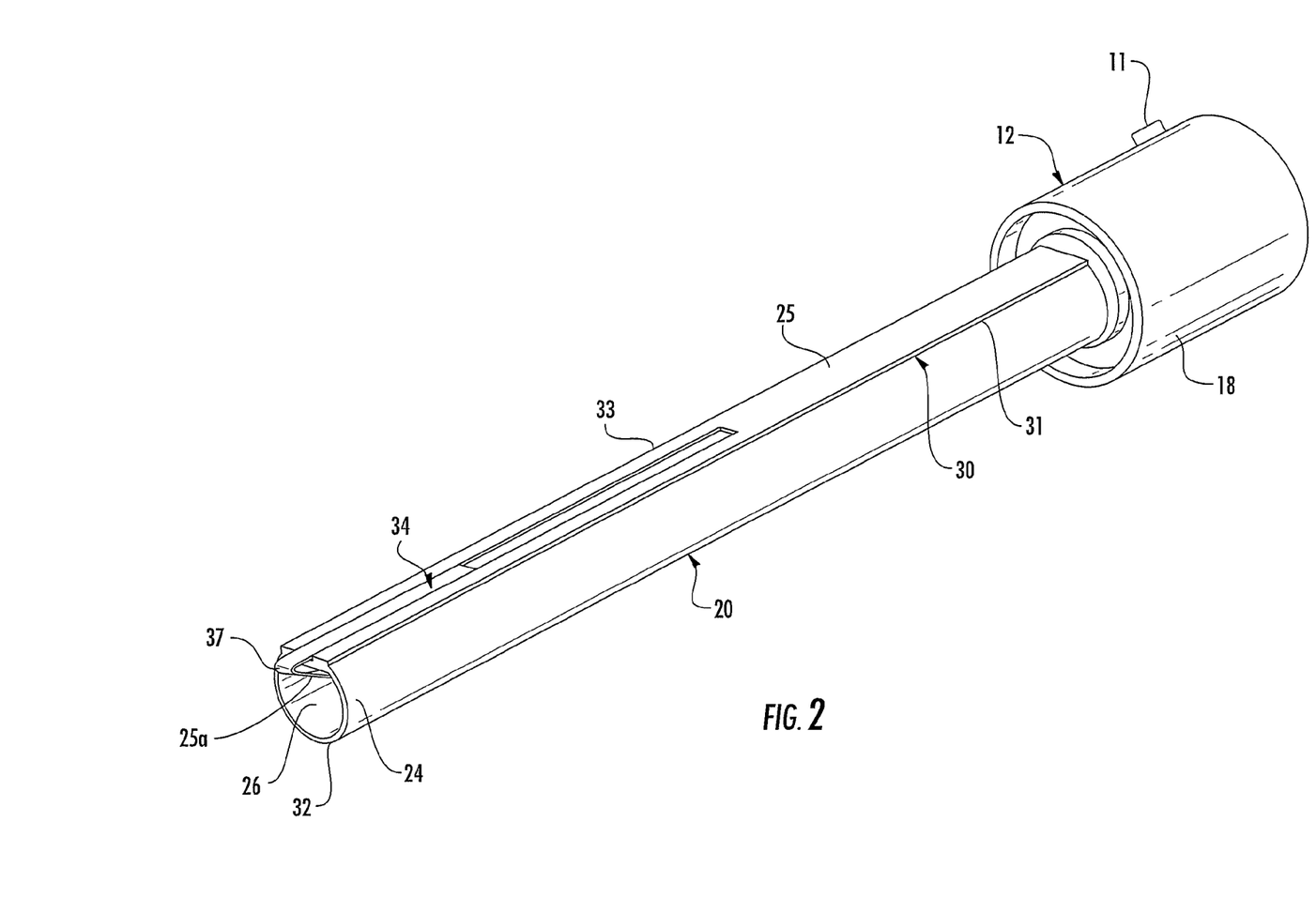
FIG. 2 is a front perspective view of the morcellator of FIG. 1.

Referring now to FIGS. 1 and 2, a bipolar morcellator 10 is provided in accordance with the present disclosure incorporating a proximal body or housing 12, an elongated tube 20, a first electrode 30, and a second electrode 34. An outer surface 18 of proximal body 12 can be sized and configured to provide a grip for a clinician's hand. Proximal body 12 defines a first lumen 16 therethrough. Proximal body 12 includes, or is coupled to, an energy source (not shown) configured to provide energy to first and second electrodes 30, 34. More specifically, proximal body 12 may house a portable generator and energy storage device, e.g., a battery, or may be configured to connect to an external source of energy, e.g., a generator connected to a power supply. Proximal body 12 can include an activation button or switch 11 to selectively deliver energy from the energy source (not shown) to electrodes 30, 34 as described in detail below.

Elongated tube 20 extends distally from proximal body 12 and defines a second lumen 26 therethrough. Second lumen 26 is axially aligned with first lumen 16 of proximal body 12. Second lumen 26 can have a diameter equal to first lumen 16 or a diameter smaller than the diameter of first lumen 16. Elongated tube 20 has a substantially circular cross-section and can include a flat upper surface 25. The outer diameter of elongated tube 20 can be 15 mm; however, larger and smaller diameters are also envisioned.

First electrode 30 is configured as the active electrode and is adapted to be electrically coupled the energy source (not shown) by any suitable known techniques. First electrode 30 can be a wire. In some embodiments, a first portion 31 of first electrode 30 extends from proximal body 12 along elongated tube 20 to a distal end 24 of elongated tube 20. A second portion 32 of first electrode 30 is positioned on part of the circumference of distal end 24. A third portion 33 of first electrode 30 extends from second portion 32 to proximal body 12 along elongated tube 20. First electrode 30 can be disposed within the wall of elongated tube 20 between distal end 24 of elongated tube 20 and proximal body 12 and/or first electrode 30 can be disposed within second lumen 26 from distal end 24 of elongated tube 20 and proximal body 12.

Second electrode 34 is configured as the return electrode and is likewise adapted to be electrically coupled to the energy source (not shown). Second electrode 34 includes a first element 37 positioned distal to second portion 32 of first electrode 30. Second electrode 34 projects proximally back into second lumen 26 of elongated tube 20. Second electrode 34 is positioned in a portion of the circumference of distal end 24 of the elongated tube 20 not covered by first electrode 30 such that the first and second electrodes 30, 34 are not in contact with each other. In some embodiments, first element 37 of second electrode 34 is positioned on flat upper surface 25 of elongated tube 20. In some embodiments, flat upper surface 25 includes a distally extending lip 25a configured to support first element 37 of second electrode 34. Second electrode 34 can be a spring material with a second element 38 biased to extend from the lip 25a towards an opposing surface on the circumference of elongated tube 20. Second element 38 of second electrode 34 can act like a leaf spring being resiliently displaced as the tissue moves through second lumen 26.

In some embodiments, first electrode 30 is configured as a metallic tube (not shown) at least partially extending from distal end 24 of elongated tube 20. The portion of the metallic tube extending from distal end 24 of elongated tube 20 can be sharpened to form blade sections. A proximal portion of the metallic tube can be coated in an insulating material such that energy is prevented from escaping from the coated portion. The proximal portion of the metallic tube can extend through second lumen 26 to proximal body 12. The metallic tube can have a slot (not shown) near the distal end sized and configured to accept second electrode 34 to be positioned at distal end 24 of elongated tube 20 such that second electrode 34 does not contact the metallic tube.

In use, morcellator 10 is positioned within a surgical site of a patient. The surgical site can be an incision in a tissue layer or a natural orifice of the body. An access port (not shown) can be inserted through the surgical site with morcellator 10 being inserted through a port of the access port. Distal end 24 of elongated tube 20 is positioned within the body of a patient near the tissue to be morcellated but not in contact with other tissue within the body of the patient. The tissue to be morcellated is brought into contact with distal end 24 of elongated tube 20. A tenaculum (not shown) can be inserted through the second lumen 26 of morcellator 10 to grasp the tissue to be morcellated and bring the tissue into contact with distal end 24.

When the tissue to be morcellated is in contact with distal end 24, morcellator 10 is activated such that energy is delivered to first and second electrodes 30, 34 to establish an electrical potential gradient therebetween. As such, energy is conducted between first and second electrode 30, 34 and through tissue disposed therebetween to cut tissue in contact with distal end 24 of elongated tube 20. Distal end 24 is configured to skive tissue from the surface to inhibit distal end 24 from plunging through the tissue. By skiving layers from the surface of the tissue, long strips of tissue can be removed as the tissue is rotated relative to morcellator 10 to continually feed tissue to morcellator 10. The morcellated tissue can be removed through the proximal end of proximal body 12.

In some embodiments, the first and/or second lumen 16, 26 include a seal (not shown) configured to maintain insufflation and/or patronal pressure during surgical procedures. The seal can also be configured to conform to a tenaculum and/or skived strip of tissue passing through the seal.

Referring to FIGS. 3-7, an oscillating morcellator 110 is provided in accordance with the present disclosure incorporating a housing 112, an elongated tube 120, and an oscillating mechanism 140. Housing 112 can include first and second body shells 112a, 112b that cooperate to house oscillating mechanism 140. First and second body shells 112a, 112b can be engaged or sealed together in any suitable fashion such as snap-fitting, screwing, welding, and/or gluing. Housing 112 can enclose a support or bracket 114.

Figures 3, 3A:
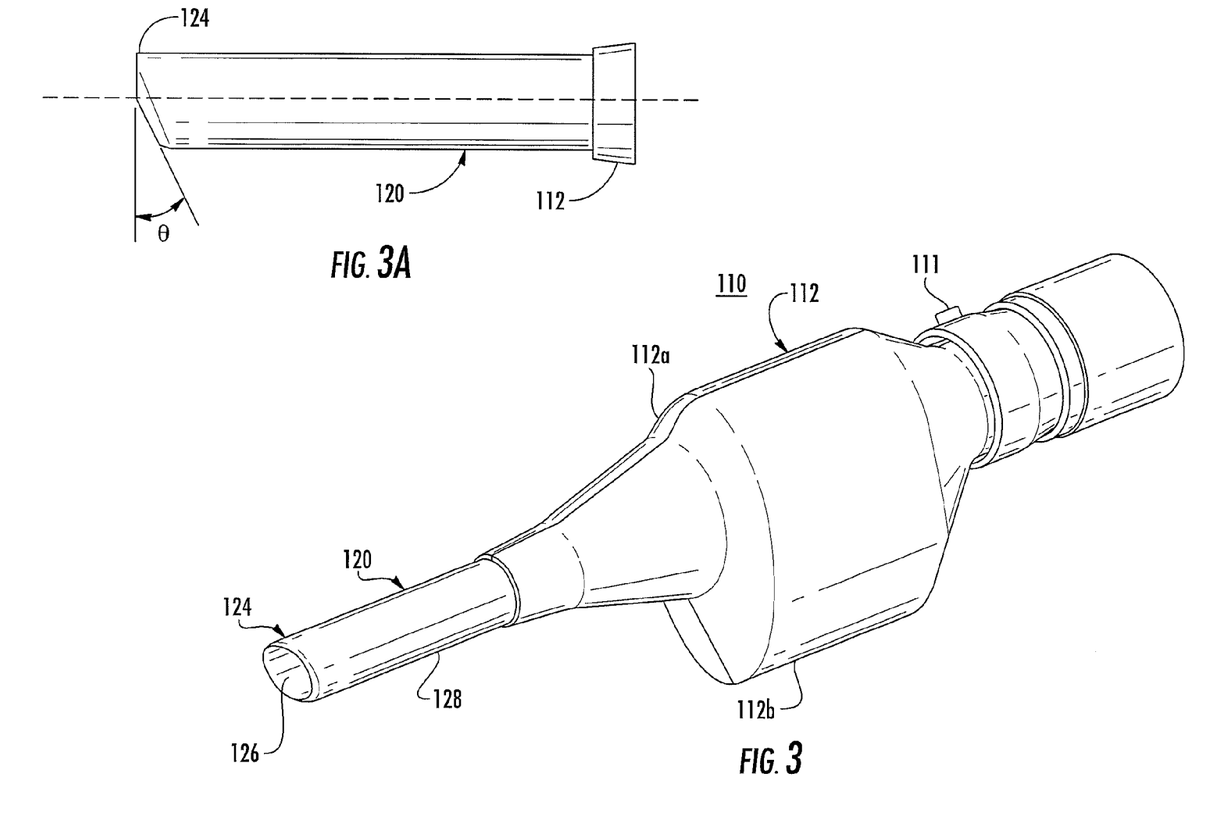
FIG. 3 is a front perspective view of another illustrative embodiment of a morcellator in accordance with the present disclosure including an oscillating mechanism.
FIG. 3A is a side view of the morcellator of the distal end of the morcellator of FIG. 3.
Figure 4:
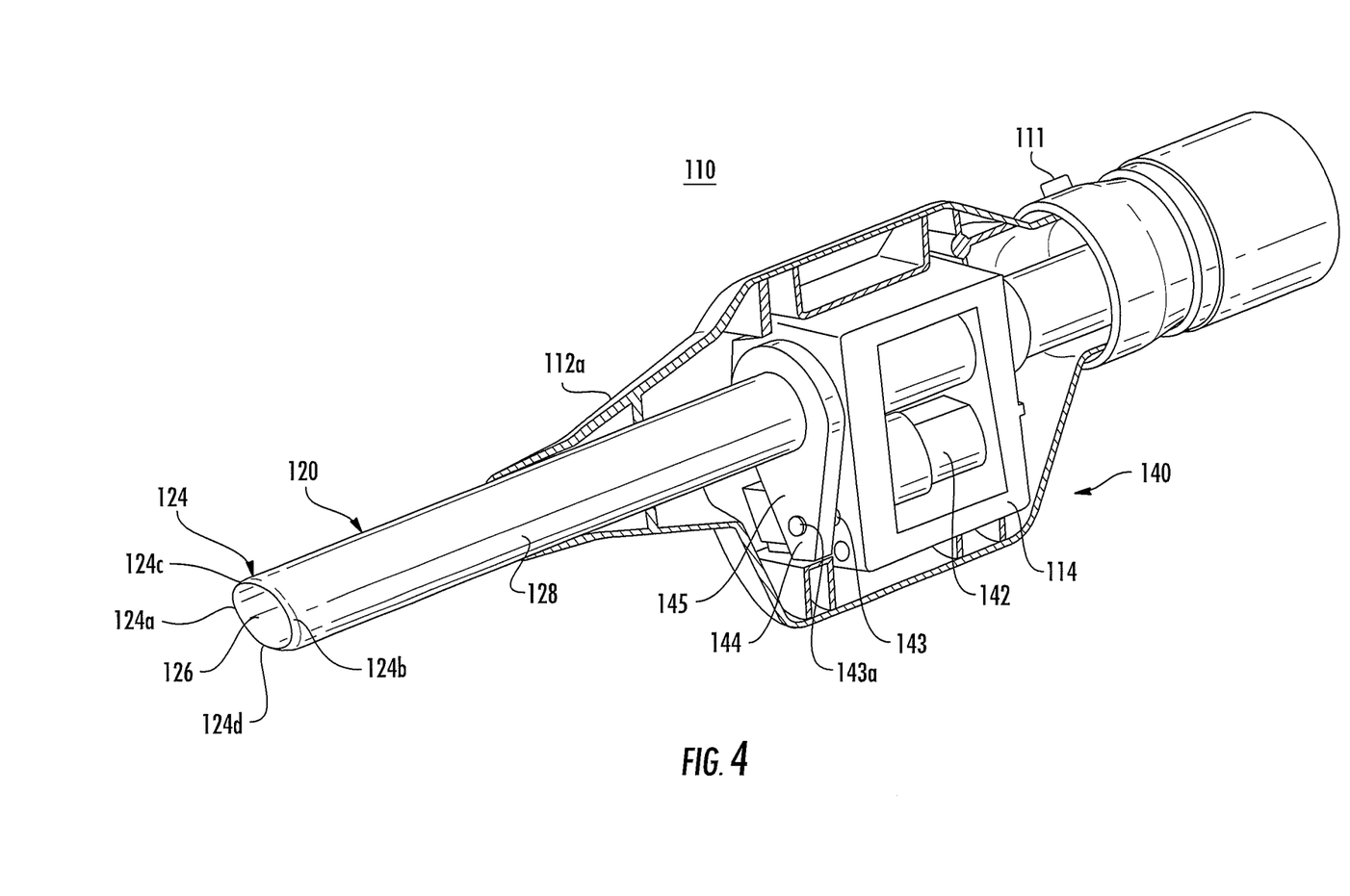
FIG. 4 is a front perspective view of the morcellator of FIG. 3 with a portion of the housing removed to show the internal components thereof.
Figure 5:
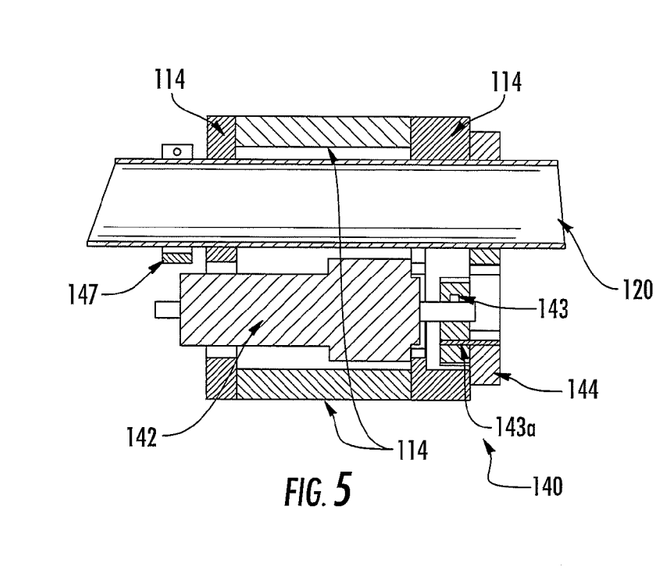
FIG. 5 is a cross-sectional view of the internal components of the housing of the morcellator of FIG. 3.
Figure 6:
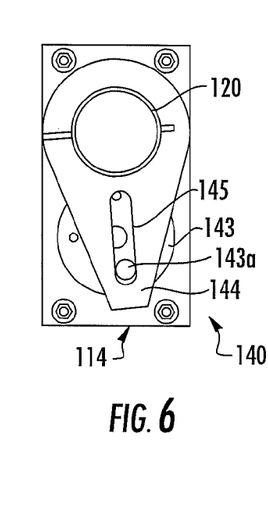
FIG. 6 is a front view of the morcellator of FIG. 3 with the housing removed.
Figure 7:
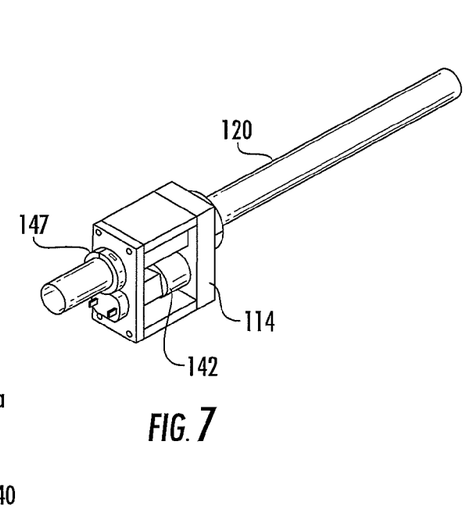
FIG. 7 is a rear perspective view of the morcellator of FIG. 3 with the housing removed.

Elongated tube 120 has a distal end 124, an outer surface 128, and a lumen 126 defined therethrough. Elongated tube 120 extends through housing 112 and couples to oscillating mechanism 140 to rotate elongated tube 120 relative to housing 112, as detailed below. Distal end 124 of elongated tube 120 extends distally from housing 112. Distal end 124 can be sharpened to form blade sections 124a, 124b. Distal end 124 can also include blunt sections 124c, 124d. Blunt sections 124c, 124d are designed in a manner to cause distal end 124 to skive along the surface rather than plunge directly through tissue. It will be appreciated that blunt sections 124c, 124d will not be damaged by contacting a tenaculum inserted through lumen 126 to grasp tissue. Other suitable configurations are also contemplated. The distal end of morcellator 110 can be disposed at an angle θ relative to a plane orthogonal to the longitudinal axis as shown in FIG. 3A. Angle θ may be any suitable angle between 0 degrees and 90 degrees.

Oscillating mechanism 140 includes a motor 142, a cam 143, and a connecting member 144. Motor 142 is mounted within housing 112 such that motor 142 and housing 112 are substantially fixed relative to each other. Motor 142 can be mounted to bracket 114. Motor 142 is mounted parallel to the longitudinal axis of elongated tube 120. Cam 143 is operatively associated with motor 142 and configured to cooperate with the rotation of motor 142.

As shown, cam 143 is directly couple to motor 142 such that cam 143 has a radial velocity equal to motor 142; however, it is also contemplated that a transmission (not shown) can be positioned between cam 143 and motor 142 such that cam 143 rotates at a radial velocity different than motor 142. Cam 143 is a disc and includes a cam pin 143a extending distally from and fixed to the surface of cam 143 near the circumference of cam 143. Connecting member 144 is fixed about the outer surface 128 of elongated tube 120 and includes a cam slot 145. Cam slot 145 is sized and configured to receive cam pin 143a. As cam 143 rotates cam pin 143a, cam pin 143a engages cam slot 145 to oscillate connecting member 144 such that elongated tube 120 oscillates about the longitudinal axis of elongated tube 120. Oscillating mechanism 140 is configured to oscillate elongated tube 120 in the range of about 200 to about 1000 cycles per minute (cpm); however, it is contemplated that oscillating mechanism 140 may be configured to cycle elongated tube 120 at higher or lower cpms. Oscillating mechanism 140 is further configured to oscillate elongated tube 120 approximately 30° about the longitudinal axis; however, it is contemplated that oscillating mechanism 140 be configured to oscillate elongated tube 120 to a greater or lesser degree. Motor 142 may be mounted perpendicular to the longitudinal axis of elongated tube 120, while the cam 143 operates in a cam slot 145 that is parallel to the longitudinal axis of elongated tube 120.

Figure 8:
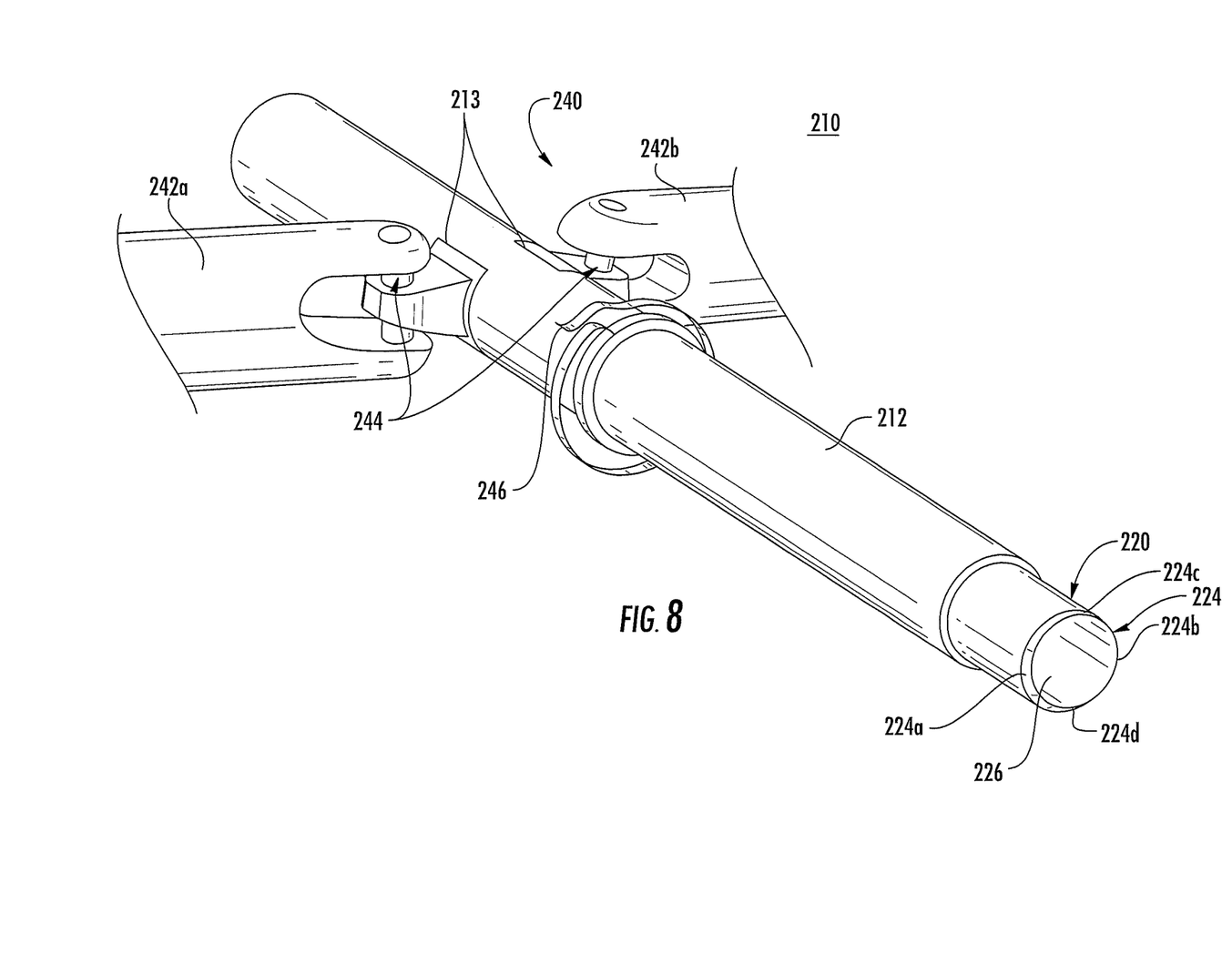
FIG. 8 is a front perspective view of another illustrative embodiment of a morcellator in accordance with the present disclosure including another oscillating mechanism.

Referring now to FIG. 8, another oscillating morcellator 210 is provided in accordance with the present disclosure incorporating a housing 212, an elongated tube or metal insert 220, and an oscillating mechanism 240. Housing 212 is constructed from a non-conductive and non-magnetic material such as a plastic. Housing 212 can include openings 213 in a proximal portion.

Metal insert 220 has a proximal end (not shown), a distal end 224, and a lumen 226 extending therebetween. Portions of distal end 224 can be sharpened to create blade sections 224a, 224b. Similar to distal end 124 of elongated tube 120, described above, portions of distal end 224 can be left blunt to form blunt sections 224c, 224d that enhance the skiving properties of metal insert 220 and provide a contact surface for a tenaculum.

Oscillating mechanism 240 includes solenoids 242a, 242b, magnets 244, and spring assembly 246. Solenoids 242a, 242b are positioned about magnets 244 such that as energy is passed through solenoids 242a, 242b each produces a magnetic field that acts on magnets 244 as described in detail below. Magnets 244 are fixed to metal insert 220 and are configured to rotate metal insert 220 in response to the magnetic fields produced by solenoids 242a, 242b. Magnets 244 can pass through openings 213 in the proximal portion of housing 212 and affix to metal insert 220. Oscillating mechanism 240 is configured to oscillate elongated tube 220 in the range of about 200 to about 1000 cycles per minute (cpm); however, it is contemplated that oscillating mechanism 240 may be configured to cycle elongated tube 220 at higher or lower cpms. Oscillating mechanism 240 is further configured to oscillate elongated tube 220 approximately 30° about the longitudinal axis; however, it is contemplated that oscillating mechanism 240 be configured to oscillate elongated tube 220 to a greater or lesser degree.

In some embodiments, oscillating mechanism 240 includes a spring assembly 246 operatively associated with metal insert 220. Spring assembly 246 has a stiffness such that cutting blade operates at or near a natural frequency controlled by the rotational inertia of metal insert 220 and the strain energy of the spring. The harmonic drive of the oscillating mechanism can be matched or tuned to the natural frequency. It will be appreciated that oscillating mechanism 140, described above, can include a similar spring assembly.

Morcellator 110 and morcellator 210 operate similarly to each other and similar to morcellator 10 described above, as such only the differences will be described in detail below. When the tissue to be morcellated is in contact with distal end 124, 224 of elongated tube 120, 220, oscillation mechanism 140, 240 is activated such that elongated tube 120, 220 oscillates to cut through the tissue in contact with the distal end 124, 224. As distal ends 124, 224 oscillate blade sections 124a, 124b and 224a, 224b, respectively, cut through the tissue while blunt sections 124c, 124d and 224c, 224d, respectively, guide distal ends 124, 224 over the surface of the tissue to skive material from the outer surface of the tissue.

Figure 9:
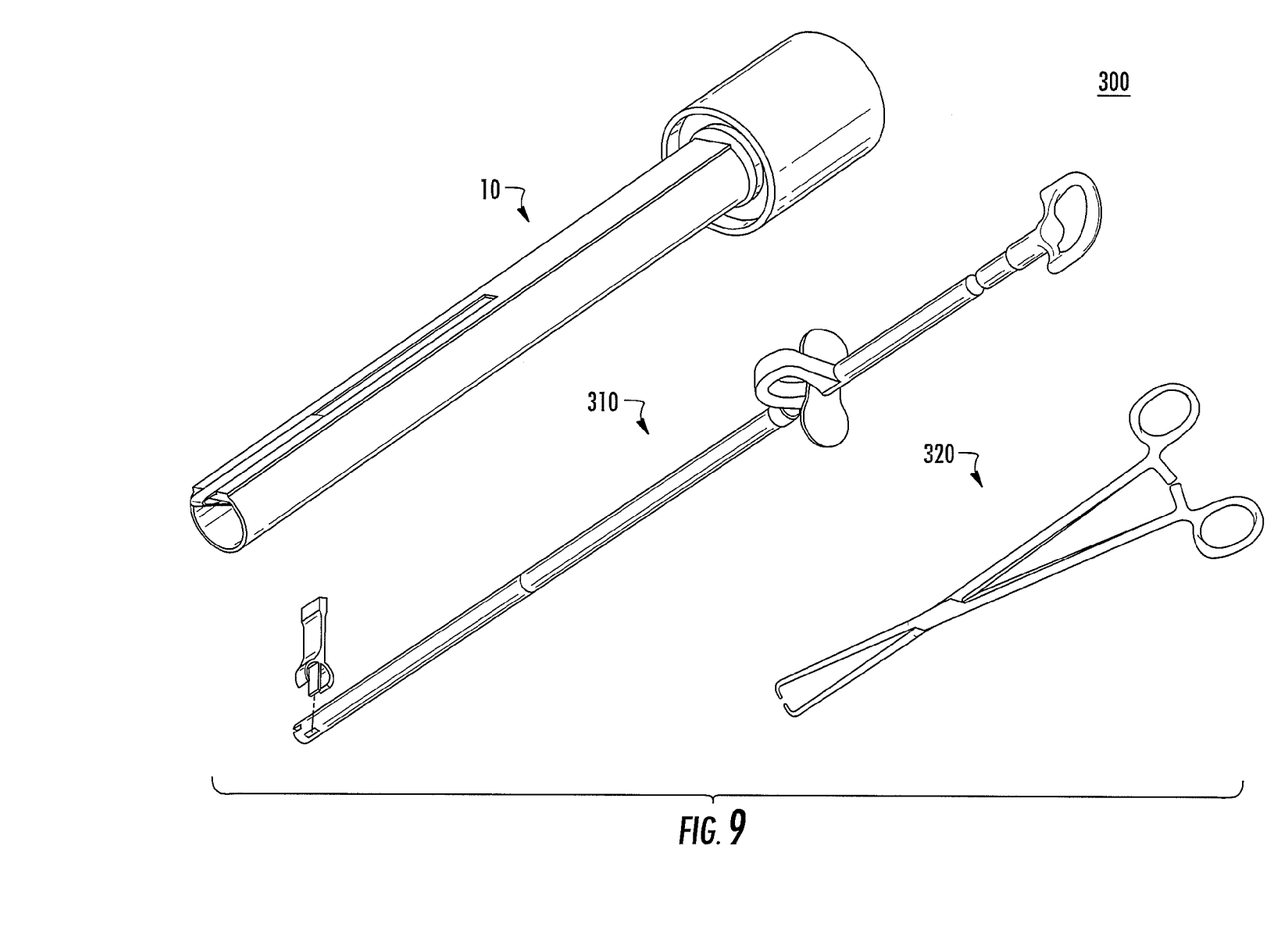
FIG. 9 is a perspective view of an illustrative embodiment of a morcellation kit in accordance with the present disclosure.

Referring to FIG. 9, a morcellation kit 300 is provided including a morcellator, a surgical retrieval apparatus 310, and a surgical instrument 320. The morcellator can be any one of or combination of morcellators 10, 110, and 210 described above. The surgical retrieval apparatus 310 can include a specimen retrieval bag (not shown) configured to encapsulate the tissue to be morcellated and to facilitate sealed removal of the tissue. An example of such a surgical retrieval apparatus is disclosed in U.S. patent application Ser. No. 13/713,075, filed Dec. 13, 2012, the contents of which are hereby incorporated by reference in their entirety. In use, the surgical retrieval apparatus 310 is configured to be inserted within the surgical site and the specimen retrieval bag deployed to encapsulate the tissue to be morcellated to substantially inhibit portions of the tissue to be morcellated from contacting and/or contaminating other tissue. The distal end of the morcellator is configured to be inserted into the specimen retrieval bag to morcellate the tissue encapsulated therein. The distal end of the morcellator and/or the specimen retrieval bag is configured to inhibit the morcellator from cutting through the specimen retrieval bag. The surgical instrument 320 is configured to feed tissue to the distal end of the morcellator, such as a tenaculum or surgical grasper.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A morcellator comprising:
   an elongated tube defining a longitudinal axis and a lumen therethrough, a distal end of the elongated tube configured to cut tissue;
   a first electrode extending from a proximal end of the elongated tube to the distal end of the elongated tube and disposed around a portion of the circumference of the distal end of the elongated tube, the first electrode adapted to electrically couple to an energy source, the first electrode defining a gap about the distal end of the elongated tube; and
   a second electrode positioned within the gap and including a first element extending distally beyond the first electrode, the second electrode adapted to couple to the energy source, wherein the second electrode is a leaf spring.

2. The morcellator of claim 1, wherein the first electrode has a first portion extending from the proximal end of the elongated tube to the distal end of the elongated tube and a second portion disposed around the portion of the circumference of the distal end of the elongated tube.

3. The morcellator of claim 2, wherein the second portion of the first electrode has a first end that is directly coupled to the first portion and a second end that is spaced apart from the first end to define the gap about the circumference of the distal end of the elongated tube between the first and second ends of the second portion.

4. The morcellator of claim 3, wherein the second electrode is positioned within the gap defined between the first and second ends of the second portion of the first electrode.

5. The morcellator of claim 3, wherein the first electrode includes a third portion extending from the distal end of the elongated tube to the proximal end thereof, the third portion directly coupled to the second end of the second portion.

6. The morcellator of claim 5, wherein the third portion extends in a direction parallel to the first portion.

7. A morcellator comprising:
   an elongated tube extending from a proximal end to a distal end thereof and defining a longitudinal axis and a lumen therethrough;
   a first electrode having a distal portion disposed about a portion of a circumference of the distal end of the elongated tube, the distal portion having a first end and a second end defining a gap therebetween about the portion of the circumference of the distal end of the elongated tube, the first electrode configured to electrically couple to an energy source; and
   a second electrode extending in a direction parallel to the longitudinal axis and disposed in the gap between the first and second ends of the distal portion of the first electrode, the second electrode configured to electrically couple to the energy source, wherein the second electrode is a leaf spring.

8. The morcellator of claim 7, wherein the elongated tube includes a flat surface extending in a direction parallel to the longitudinal axis.

9. The morcellator of claim 8, wherein the second electrode includes a first element that is positioned on the flat surface of the elongated tube.

10. The morcellator of claim 9, wherein the second electrode includes a second element that extends from a portion of the first element extending beyond a distal end elongated tube and into the lumen of the elongated tube.

* * * * *